United States Patent [19]

Tanaka

[11] Patent Number: 5,728,563
[45] Date of Patent: Mar. 17, 1998

[54] CYCLIC NUCLEOTIDE PHOSPHODIESTERASE AND A METHOD FOR PRODUCTION THEREOF

[75] Inventor: Toshio Tanaka, Mie, Japan

[73] Assignee: Taisho Pharmaceutical Co., Ltd., Japan

[21] Appl. No.: 481,442

[22] PCT Filed: Jan. 28, 1994

[86] PCT No.: PCT/JP94/00121

§ 371 Date: Jan. 21, 1995

§ 102(e) Date: Jan. 21, 1995

[87] PCT Pub. No.: WO94/17181

PCT Pub. Date: Aug. 4, 1994

[30] Foreign Application Priority Data

Jan. 29, 1993 [JP] Japan .................. 5-013150

[51] Int. Cl.$^6$ .................. C12N 9/14; C12N 9/16; C12P 19/30; C12P 1/00
[52] U.S. Cl. .................. 435/196; 435/195; 435/41; 435/89
[58] Field of Search .................. 435/196, 195, 435/41, 89

[56] References Cited

FOREIGN PATENT DOCUMENTS 9218541 10/1992 WIPO .

OTHER PUBLICATIONS

66th Annual Mtg. of Japanese Pharm. Soc. Mar. 24–27, 1993, Abstract No. P573.
BR. J. Pharmacol (1994) 389–90, 1994.
Molecular Pharmacology, 29:506–514.
The Journal of Biological Chemistry, Col 263, No. 30, Issue of Oct. 25, 1988, pp. 15681–15687.
Mukai et al. Br. J. Pharmacol. vol. 111(2) 1994 pp. 389–390 –Abstract Enclosed.
Appleman et al. J. Biol. Chem vol. 246, pp. 3145–3150, 1971.
Kakiuchi et al. J. Biochem. vol. 146, pp. 109–120, 1975 Abstract.
Shinshi et al. Biochem. vol. 15, pp. 2185–2190, 1976 –Abstract.
Morishima. Biochim et. Biophy. ACTA vol. 410, pp. 310–317, 1975 –Abstract.

Primary Examiner—Leon B. Lankford, Jr.
Assistant Examiner—Christohpher R. Tate
Attorney, Agent, or Firm—Lorusso & Loud

[57] ABSTRACT

A novel cyclic nucleotide phosphodiesterase, which is different from known isozyme families, is isolated and purified from rat cerebrum. This enzyme has the following physicochemical properties (1) to (3). (1) The enzyme acts on cAMP to form 5'-AMP and on cGMP to form 5'-GMP; (2) The Km values for cAMP and cGMP are 0.11 µM and 1.78 µM, respectively, as indicating substrate specificity; and (3) the molecular weight is approximately 298000.

3 Claims, 4 Drawing Sheets

CYCLIC NUCLEOTIDE PHOSPHODIESTERASE AND A METHOD FOR PRODUCTION THEREOF

FIELD OF THE INVENTION

The present invention relates to a novel cyclic nucleotide phosphodiesterase and a method for production thereof.

BACKGROUND ART

Cyclic adenosine 3',5'-monophosphate (cAMP) and cyclic guanosine 3',5'-monophosphate (cGMP) have been found to be intracellular messenger so that their importance in regulating various cell functions has been revealed. Cyclic nucleotide phosphodiesterases are known as enzymes for degrading cAMP or cGMP and play an important role in vivo involving cyclic nucleotide metabolism. Accordingly, inhibition of cyclic nucleotide phosphodiesterases by chemicals seriously affects the cyclic nucleotide metabolism, resulting eventually in change in cell functions.

Five isozyme families from I to V are currently reported of the cyclic nucleotide phosphodiesterase, each family composed of several subtypes (Tanaka et al., Folia pharmacol. japon., 100, 249–258, 1992).

In recent years, cyclic nucleotide phosphodiesterase inhibitors have been developed as new drugs. In order to screen such inhibitors and clarify their mechanism, analysis on a selective inhibition activity against the cyclic nucleotide phosphodiesterase is important as a basis for the development.

An object of the present invention is to provide a novel cyclic nucleotide phosphodiesterase for the purpose of developing a new drug.

SUMMARY OF THE INVENTION

In view of the foregoing object, extensive studies have been made; as a result, the present inventor has discovered a novel cyclic nucleotide phosphodiesterase in animal organs or tissues, which is dissimilar to known isozyme families. For the first time, the present inventor has isolated and purified the enzyme and clarified its properties.

The present invention is directed to a cyclic nucleotide phosphodiesterase characterized by at least the following physicochemical properties (1) through (7) (hereinafter simply referred to as the enzyme of the present invention). The present invention is also directed to a method for producing the enzyme which comprises excising animal organs or tissues and eluting the resulting homogenate with a linear gradient elution technique using a Mono-Q HR ion exchange column.

(1) Activity:
The enzyme acts on cAMP and cGMP to form 5'-AMP and 5'-GMP, respectively.

(2) Substrate specificity:
The Km values for cAMP and cGMP show 0.11 μM and 1.78 μM, respectively.

(3) Optimum pH:
The optimum pH for cAMP hydrolysis is 10.

(4) Thermal stability:
The initial velocities of the enzymatic activity at 37° C. are greater than those at 30° C. The enzymatic activity is lost by heating at 60° C. for 10 minutes.

(5) Effects of inhibitors:
$IC_{50}$ is >300 μM with nicardipine, >300 μM with Cilostazol and 5-(4-acetamidophenyl)pyrazin-1H-one (SK&F94120), and >300 μM with rolipram and 4-(3-buthoxy-4-methoxybenzyl)-2-imidazolidinone (Ro20-1724). The enzyme is calcium-calmodulin-insensitive and cGMP-insensitive.

(6) Effect of metal ions:
Magnesium is the most efficient metal cation for the enzyme of the present invention.

(7) Molecular weight:
298000±8000 (Superose 12HR 10/30, gel filtration)

BEST MODE FOR CARRYING OUT THE INVENTION

According to the present invention, the enzyme of the present invention is widely found particularly in mammalian brains and also distributed in animal organs or tissues such as cardiac muscle, lung, kidney, smooth muscle or platelet, which can produce cyclic nucleotide phosphodiesterases.

The enzyme of the present invention can be isolated and purified by excising animal organs or tissues, homogenizing, filtering the supernatant from the homogenate by ultracentrifugation through glass wool, applying the filtrate to ion exchange column chromatography using, e.g., a Q-Sepharose Fast Flow anionic exchange column, and using a calmodulin-Sepharose affinity column, and then eluting the column by a linear gradient technique. The method for production of the enzyme according to the present invention is characterized by using a Mono-Q HR ion exchange column and thus, the enzyme of the present invention has been found for the first time. Therefore, the rest of the steps like the excision organs or tissues, homogenization, ultracentrifugation and elution are immaterial to the present invention at all. These steps may be those conventionally employed in the art.

The activity of the enzyme of the present invention was determined by the two-step assay (Masuoka et al., Biochem. Biophys. Res. Commun., 169, 315–322, 1990). In some experiments cAMP hydrolysis was determined in the presence of 10 μM cGMP or 0.4 μg/ml calmodulin plus 0.2 mM $CaCl_2$, instead of ethyleneglycol bis(2-aminoethyl ether) tetraacetic acid (EGTA).

Next, the physicochemical properties of the enzyme of the present invention are given below.

(1) Activity:
The enzyme of the present invention is reacted with [8-$^3$H] cAMP and [8-$^3$H] cGMP as a substrate to form [8-$^3$H] 5'-adenosine monophosphate (5'-AMP) and [8-$^3$H] 5'-guanosine monophosphate (5'-GMP), respectively.

5'-Nucleotidase acts on the products to form [8-$^3$H] adenosine and [8-$^3$H] guanosine, respectively.

As isozyme families of cyclic nucleotide phosphodiesterase, five subtypes are known (hereinafter these subtypes are referred to as PDEI, PDEII, PDEIII, PDEIV and PDEV, respectively). It is also known that among these subtypes, PDEIV and PDEV sparingly hydrolyze cGMP and cAMP, respectively. From the fact it is concluded that the enzyme of the present invention is dissimilar to any of PDEIV and PDEV.

(2) Substrate specificity:

By varying concentrations of cAMP or cGMP as a substrate, the enzyme of the present invention is assayed for the enzymatic activity. A Km value is determined by double reciprocal plots. The results reveal that Km values for cAMP and cGMP are 0.11 μM (0.109±0.008 μM) and 1.78 μM (1.78±0.042 μM), respectively, indicating that the enzyme of the present invention is highly specific to cAMP.

Figure 1:
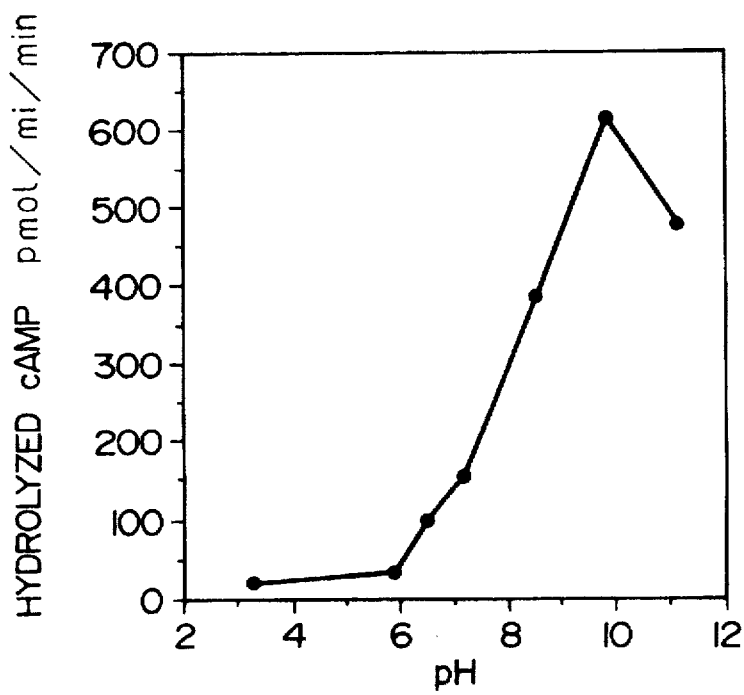
FIG. 1 shows relationship between pH and the enzymatic activity of the present enzyme.

(3) Optimum pH:

FIG. 1 shows the relationship between pH and the enzymatic activity of the present enzyme when 50 mM Tris hydrochloride buffer containing 5 mM magnesium chloride, $MgCl_2$, was used. The maximum activity was observed at pH of 10.

Figure 2:
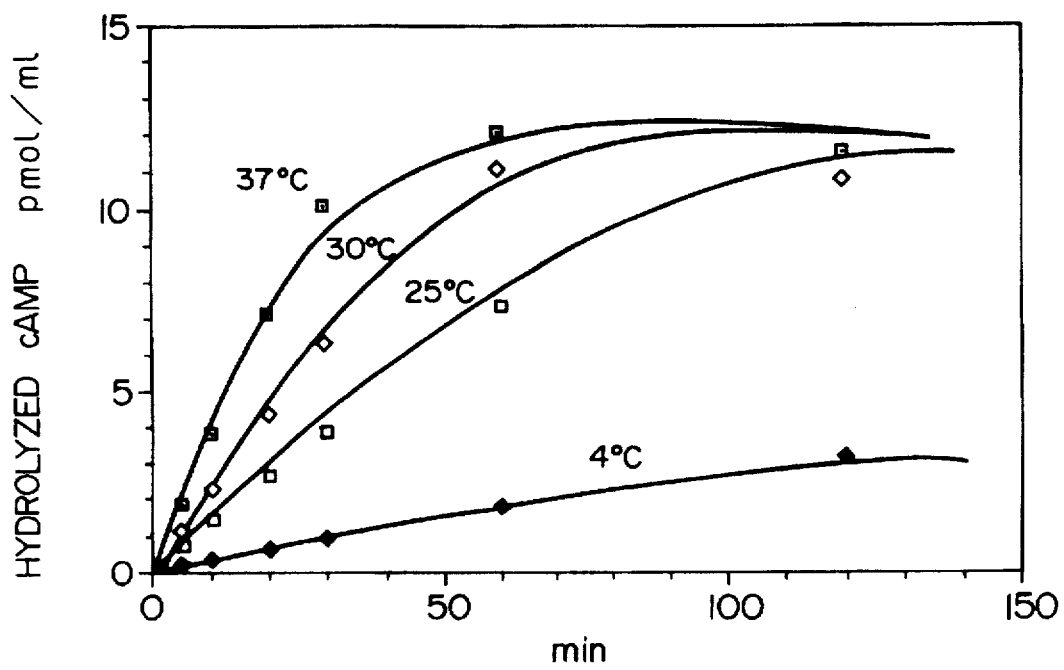
FIG. 2 shows effects of temperature on the enzymatic activity of the present enzyme.
Figure 3:
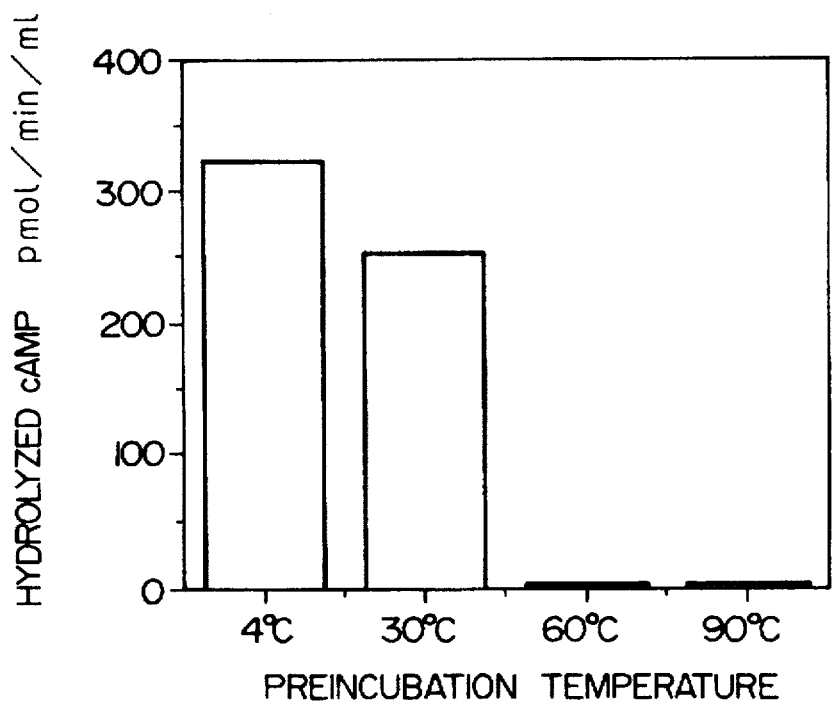
FIG. 3 shows effects of temperature on the enzymatic activity of the present enzyme.

(4) Thermal stability:

Effects on the enzyme of the present invention was studied at temperatures of 4° C., 25° C., 30° C. and 37° C. FIG. 2 shows that the initial velocities of the enzymatic activity at 37° C. are greater than those at temperatures below 30° C. The enzymatic activity was obviously lost by heating at 60° C. or 90° C. for 10 minutes, see FIG. 3.

(5) Effects of inhibitors:

Using various inhibitors which are known to inhibit the activity of PDEI, III or IV, the enzymatic activity of the enzyme of the present invention was measured by varying the concentration of these inhibitors. $IC_{50}$ was determined when the enzymatic activity was made 100% in the absence of an inhibitor.

$IC_{50}$ of nicardipine as a PDEI inhibitor is >300, $IC_{50}$ of cilostazol and SK&F94120 (PDEIII inhibitor) is >300 μM, and $IC_{50}$ of rolipram and Ro20-1724 (PDEIV inhibitor) is >300 μM. $IC_{50}$ of 3-isobutyl-1-methylxanthine (IBMX) which is a non-selective inhibitor is 26.5 μM (26.5±2.5 μM). The inhibition constant (Ki value) of papaverine which is a non-selective inhibitor is 0.036 μM. Herein, the inhibition constant was determined by varying concentrations of cAMP as a substrate and papaverine as an inhibitor and applying Dixon plots of data from the thus obtained enzymatic activity.

The results reveal that the enzyme of the present invention is less inhibited by nicardipine as compared to PDEI, and not inhibited by SK&F94120 or cilostazol as compared to PDEIII; the present invention is less inhibited by rolipram or Ro20-1724, as compared to PDEIV.

Effects on the enzyme of the present invention were analyzed by adding 0.4 μg/ml calmodulin purified from bovine brain and 0.2 mM calcium chloride. No significant difference in the enzymatic activity of the enzyme of the present invention was appreciated between in the presence of PDEI activator calcium-calmodulin and in the presence of 2 mM EGTA as a calcium chelating agent.

The enzyme of the present invention is not activated by calcium-calmodulin. Therefore, the enzyme of the present invention is different from PDEI activated by calcium-calmodulin.

The enzyme of the present invention is not activated by cGMP and thus different from PDEII which is activated by cGMP.

Figure 4:
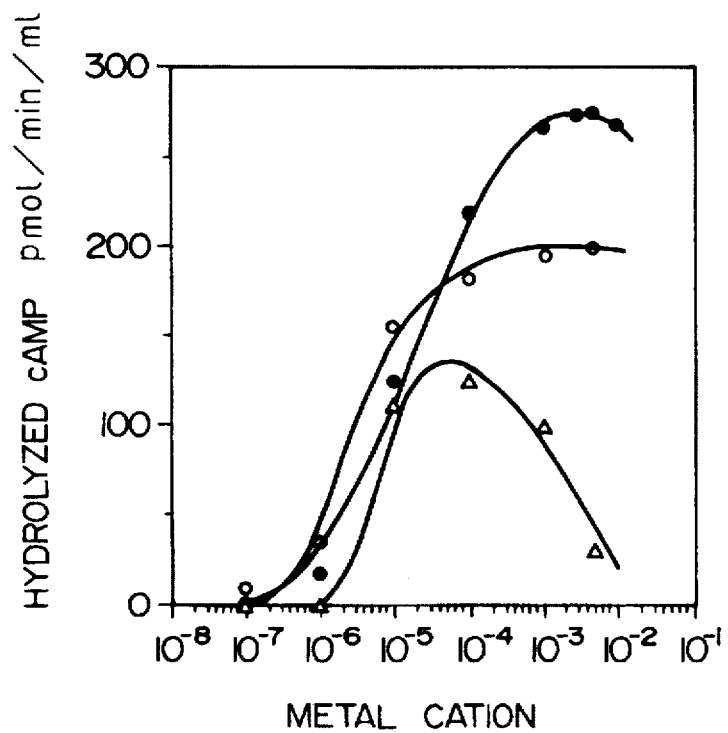
FIG. 4 shows effects of metal ions on the enzymatic activity of the present enzyme.

(6) Effect of metal ions:

Magnesium is the most efficient metal cation for the enzyme of the present invention. The maximum effect was observed at concentrations over 5 mM, see FIG. 4. Manganese had a relatively stimulatory effect. $Co^{2+}$ had an inhibitory effect at concentrations above 100 μM and a stimulatory effect at concentrations of less than 100 μM. $Zn^{2+}$, $Cu^{2+}$, $Ca^{2+}$, $Ni^{2+}$ and $Ba^{2+}$ showed no ability as a cofactor for the enzymatic reaction.

(7) Molecular weight:

The molecular weight was determined from the eluted position of the enzyme of the present invention on Superose 12HR 10/30 (Pharmacia: column size of 10 mm ×300 mm) which had been equilibrated with 0.05 M phosphate buffer, pH 7.1, and 0.15 M sodium chloride, using a molecular weight marker for gel filtration. The molecular weight was found to be 298000±8000.

Hereinafter the present invention is described in more detail, by referring to the examples and experiments.

EXAMPLE

Figure 5:
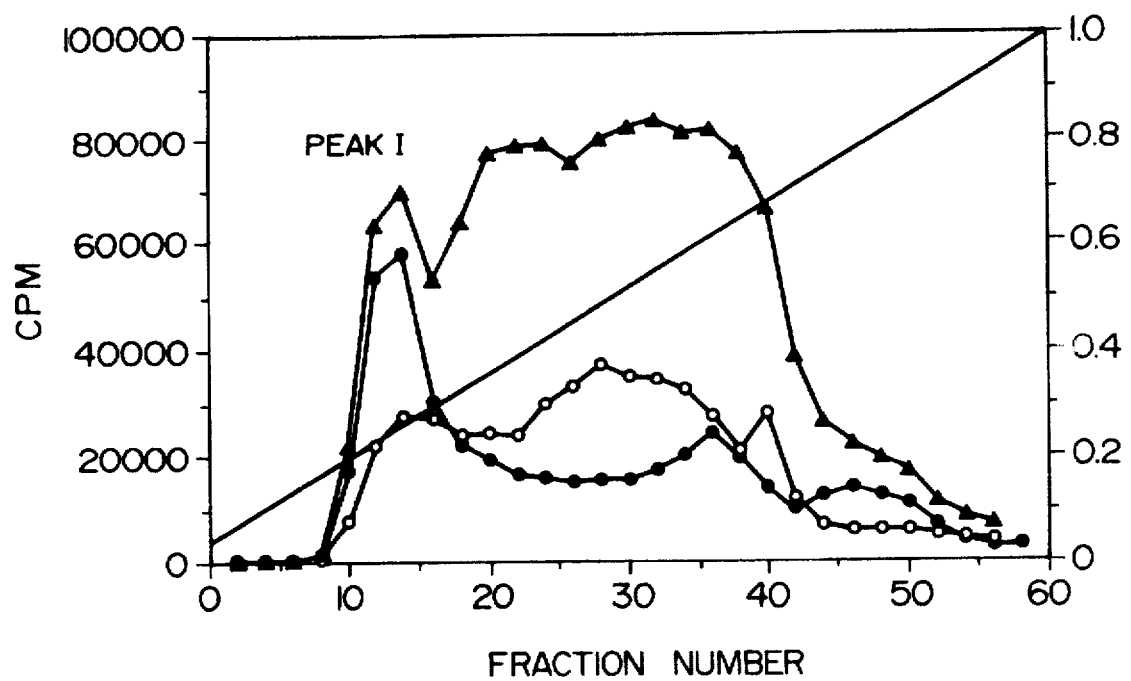
FIG. 5 shows relationship between the fraction and the enzymatic activity, when applied to a Q-Sepharose Fast Flow anionic exchange column.

Isolation of cyclic nucleotide phosphodiesterase from the rat cerebrum (1) Ten grams of cerebral cortex were excised from rats and rinsed several times in ice-cold homogenization Buffer A (50 mM Tris-hydrochloride, pH 7.5, 0.25 M sucrose, 0.1 mMEGTA, 0.1 mM dithiothreitol, 20 μM leupeptin, 10 μg/ml soybean trypsin inhibitor, 10 μg/ml pepstatin, 10 μg/ml chymostatin and 1 μM (p-amidinophenyl) methanesulfonyl fluoride hydrochloride (pAPMSF). The tissue was gently homogenized, with a Potter S homogenizer, in 8–10 volumes of Buffer A. The cerebral homogenate was then centrifuged at 100,000 x g for 60 minutes. The resultant supernatant containing cytosolic cyclic nucleotide phosphodiesterase was filtered through glass wool and then through a cellulose acetate 0.20 μm-filter unit (Toyo Filter Paper Co., Ltd.). The filtered supernatant was applied to a Q-Sepharose Fast Flow (Pharmacia LKB Biotechnology) anion exchange column of 1.6×20 cm at a flow rate of 1.0 ml/min, after the column had been equilibrated with Buffer B (30 mM sodium acetate, pH 7.2, 0.1 mM dithiothreitol and 1 μM pAPMSF. The loaded column was washed with 300 ml of Buffer B. The cytosolic cyclic nucleotide phosphodiesterase was then eluted with a 420 ml-gradient of sodium acetate (0.03–1.0 M) in the Buffer B, at a flow rate of 1.0 ml/min. Fractions of 7 ml each were collected during the entire elution. FIG. 5 shows its elution profile.

Figure 6:
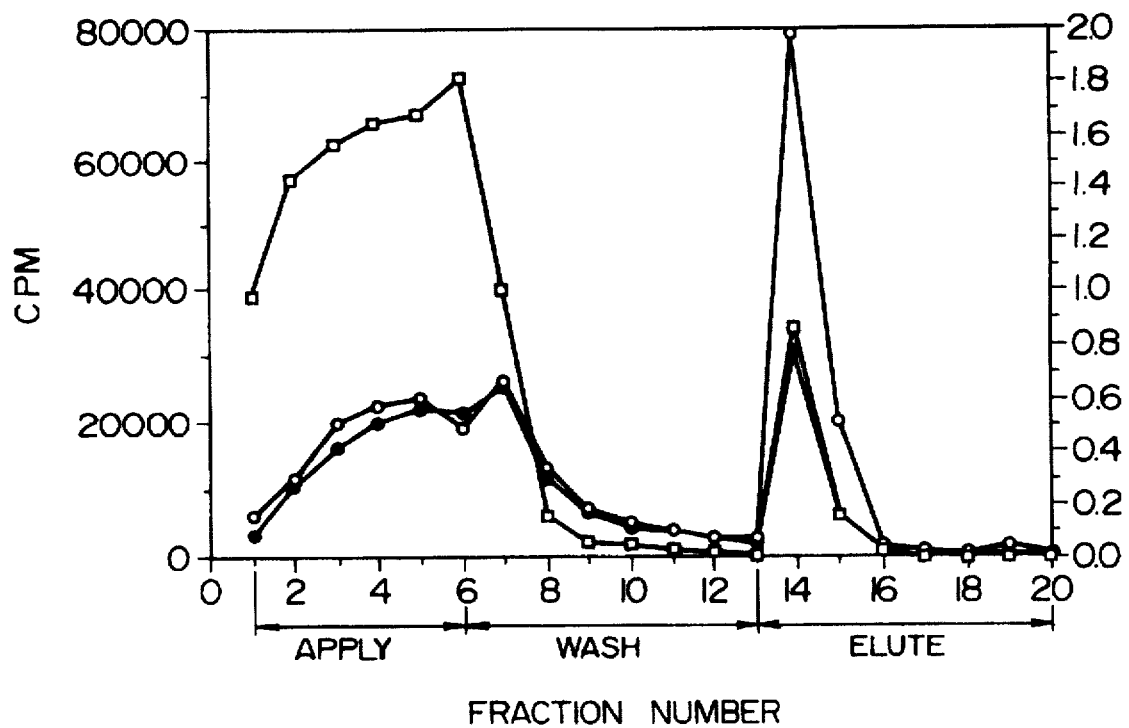
FIG. 6 shows relationship between the fraction and the enzymatic activity, when applied to a calmodulin-Sepharose affinity column.

(2) To further purify the fractions containing the enzyme of the present invention isolated from the Q-Sepharose Fast Flow column, fractions 10 through 17 were pooled, concentrated and applied to a calmodulin-Sepharose affinity column in the presence of excess $Ca^{2+}$ (2 mM). The calmodulin-insensitive proteins which did not bind to the colum, containing the enzymatic activity of the enzyme of the present invention, were eluted from the column with 27 ml of the equilibration buffer (Buffer C: 20 mM Tris-HCl, pH 7.5, 0.15 M NaCl, mM $MgCl_2$, 2 mM $CaCl_2$, 0.1 mM EGTA, 1 mM dithiothreitol, 1 μM pAPMSF. FIG. 6 shows its elution profile.

(3) The eluate (fractions 1 through 6) was dialyzed against Buffer D (50 mM Tris-HCl, pH 7.5, 0.1 mM EGTA, 0.1 mM dithiothreitol and 1 μM pAPMSF) overnight, and then applied to a Mono-Q HR10/10 column anion exchange column (Pharmacia) at a flow rate of 0.5 ml/min, after the column had been equilibrated with Buffer D. The loaded column was washed with 80 ml of Buffer D. The enzyme of the present invention was then eluted with a 50 ml-linear gradient of sodium chloride (0–0.15 M) in Buffer D, at a flow rate of 0.15 ml/min. Fractions of 2 ml each were Collected.

Figure 7:
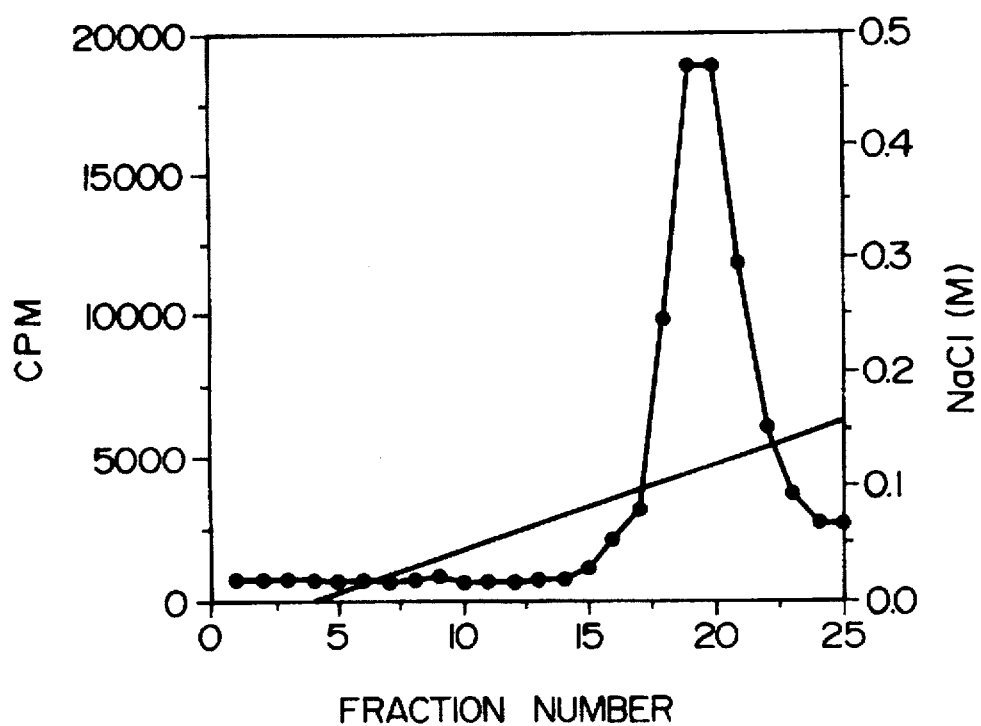
FIG. 7 shows relationship between the fraction and the enzymatic activity, when applied to a Mono Q HR10/10 anionic exchange column.

FIG. 7 shows its elution profile. The maximum activity of the enzyme of the present invention was observed in fractions 19 and 20.

In the isolation and purification of the enzyme of the present invention described above, the enzymatic activity was determined by the following two-step assay.

Assay for the enzymatic activity

The reaction mixture containing 50 mM Tris-HCl, pH 8.0, 5 mM $MgCl_2$, 2 mM EGTA and 0.1 mg/ml bovine serum albumin in 0.5 ml of the total amount is added with the enzyme of the present invention isolated and further with [8-$^3$H] cAMP. The mixture is reacted at 30° C. Ten minutes after, the reaction mixture is put in a heat bath of 100° C. to terminate the reaction in 5 minutes. That is, the enzyme of the present invention is inactivated by heating at 100° C. A test tube charged with the reaction mixture is then ice-cooled. Next, 50 µg of snake venom, which contains 5'-nucleotidase, is added to and reacted with the reaction mixture at 30° C. for 10 minutes. As the result, [8-$^3$H] cAMP is decomposed with the enzyme of the present invention to form [8-$^3$H] 5'-AMP, which is then with 5'-nucleotidase in snake venom to form [8-$^3$H] adenosine. After 4 ml of water is added to this reaction mixture, the mixture is adsorbed onto a column packed with cation exchange resin (AG50 WX4, Bio-Rad). After thoroughly rinsing, the reaction product [8-$^3$H] adenosine is eluted with 1.5 ml 3N $NH_4OH$. The radioactivity of the eluted [8-$^3$H] adenosine is measured to determine the enzymatic activity of the present invention.

Experiment 1. Function

The enzyme of the present invention isolated and purified from rat cerebral cortex in Example was acted on [8-$^3$H] cAMP and [8-$^3$H] cGMP as substrates to form [8-$^3$H] 5'-AMP and [8-$^3$H] 5'-GMP, respectively. The products were reacted with 5'-nucleotidase to form [8-$^3$H] adenosine and [8-$^3$H] guanosine, respectively. These products were separated from each other on a cation exchange resin column (AG50 W-X4, Bio-Rad) to assay for the radioactivity. The assay was carried out in a manner similar to that of the enzymatic activity described in Example.

Experiment 2. Substrate specificity

By varying concentrations of cAMP or cGMP as a substrate in the range of 0.06 µM to 100 µM, the enzymatic activity of the present invention was assayed in a manner similar to that of the enzymatic activity described in Example. A Km value was determined by double reciprocal plots. The results reveal that Km values for cAMP and cGMP are 0.11 µM (0.109±0.008 µM) and 1.78 µM (1.78±0.042 µM), respectively, indicating that the enzyme of the present invention is highly specific to cAMP.

Experiment 3. Optimum pH

A definite amount of the enzyme of the present invention and substrate cAMP were added to a 50 mM Tris-HCl buffer mixture having various pH values. The enzymatic activity was determined in a manner similar to the procedures described in Example.

FIG. 1 shows the relationship between pH and the enzymatic activity of the present enzyme when 50 mM Tris hydrochloride buffer containing 5 mM magnesium chloride, $MgCl_2$, was used. The maximum activity was observed at pH of 10.

Experiment 4. Thermal stability

Effects on the enzyme of the present invention was studied at temperatures of 4° C., 25° C., 30° C. and 37° C., in a manner similar to the procedures assaying for the enzymatic activity described in Example. FIG. 2 shows that the initial velocities of the enzymatic activity at 37° C. are greater than those at temperatures below 30° C. The enzymatic activity was obviously lost by heating at 60° C. or 90° C. for 10 minutes, see FIG. 3.

Experiment 5. Effects of inhibitors

The enzymatic activity of the enzyme of the present invention was measured by varying the concentrations of various inhibitors. $IC_{50}$ was determined when the enzymatic activity was made 100% in the absence of an inhibitor. In more detail, during the reaction with the enzyme of the present invention in assaying for the enzymatic activity described in Example, an inhibitor having various concentrations was further added to the reaction mixture to determine the enzymatic activity.

$IC_{50}$ of nicardipine is >300, $IC_{50}$ of cilostazol and SK&F94120 is >300 µM, and $IC_{50}$ of rolipram and Ro20-1724 is >300 µM. $IC_{50}$ of IBMX is 26.5 µM (26.5±2.5 µM). The inhibition constant (Ki value) of papaverine which is a non-selective inhibitor is 0.036 µM. Herein, the inhibition constant was determined by varying concentrations of cAMP as a substrate and papaverine as an inhibitor and applying Dixon plots of data from the thus obtained enzymatic activity.

Effects on the enzyme of the present invention were analyzed by adding 0.4 µg/ml calmodulin purified from bovine brain and 0.2 mM calcium chloride. No significant difference in the enzymatic activity of the enzyme of the present invention was noted between in the presence of PDEI activator calcium-calmodulin and in the presence of 2 mM EGTA as a calcium chelating agent.

Experiment 6. Effect of metal ions

The enzymatic activity of the present invention was determined in a manner similar to that of Example, by varying the concentration of 5 mM $MgCl_2$ in the reaction mixture. As the result, the enzyme of the present invention was activated by 1 µM ($1 \times 10^{-6}$) $MgCl_2$ and the maximum activity was observed at concentrations over 5 mM ($5 \times 10^{-3}$), see FIG. 4.

Manganese had a relatively stimulatory effect. $Co^{2+}$ had an inhibitory effect at concentrations above 100 µM and a stimulatory effect at concentrations of less than 100 µM. $Zn^{2+}$, $Cu^{2+}$, $Ca^{2+}$, $Ni^{2+}$ and $Ba^{2+}$ showed no ability as a cofactor for the enzymatic reaction.

Experiment 7. Molecular weight

The molecular weight was determined from the eluted position of the enzyme of the present invention on Superose 12HR 10/30 (Pharmacia: column size of 10 mm ×300 mm) which had been equilibrated with 0.05 M phosphate buffer, pH 7.1, and 0.15 M sodium chloride, using a molecular weight marker for gel filtration. The molecular weight was found to be 298000±8000.

Industrial Applicability:

A novel cyclic nucleotide phosphodiesterase has been found by the present invention. Several enzyme inhibitors have been developed as new drugs. The present invention has enabled to develop drugs and, has provided screening for analysis of a selective inhibitory action of the cyclic nucleotide phosphodiesterase and has enabled to clarify the mechanism, which is a basis for development of drugs.

I claim:

1. An isolated and purified cyclic nucleotide phosphodiesterase having the following physicochemical properties:

(a) activity:

the enzyme acts on 3',5'-cAMP and 3', 5'-cGMP to form 5'-AMP and 5'-GMP, respectively;

(b) substrate specificity:

the Km values for cAMP and cGMP show 0.11 µM and 1.78 µM, respectively;

(c) substrate pH:

the optimum pH for cAMP hydrolysis is 10 at 30° C.;

(d) thermal stability:

the initial velocities of the enzymatic activity at 37° C. are greater than those at 30° C.; the enzymatic activity is lost by heating at 60° C. for 10 minutes;

(e) effects of inhibitors:

$IC_{50}$ is >300 µM with nicardipine, >300 µM with cilostazol and 5-(4-acetamidophenyl)pyrazin-1H-one (SK&F94120), and >300 µM with rolipram and 4-(3-buthoxy-4-methoxybenzyl)-2-imidazolidinone (Ro20-1724); the enzyme is calcium-calmodulin-insensitive and cGMP- insensitive;

(f) effect of metal ions:

magnesium is the most efficient metal cation for the enzyme of the present invention; and (g) molecular weight:

298000±8000 (Superose 12HR 10/30, gel filtration).

2. A method for producing a cyclic nucleotide phosphodiesterase according to claim 1, comprising:

excising an animal organ or tissue;

homogenizing the excised organ or tissue to produce a homogenate;

separating a supernatant containing the cyclic nucleotide phosphodiesterase from said homogenate;

separating the cyclic nucleotide phosphodiesterase from said supernatant by passing said supernatant through a Mono-Q HR ion exchange column;

eluting the cyclic nucleotide phosphodiesterase from said ion exchange column to obtain a series of fractions; and recovering said cyclic nucleotide phosphodiesterase from a selected number of said fractions.

3. A method according to claim 2 wherein mammalian brain tissue is excised.

* * * * *

UNITED STATES PATENT AND TRADEMARK OFFICE
CERTIFICATE OF CORRECTION

PATENT NO. : 5,728,563
DATED : March 17, 1998
INVENTOR(S) : Toshio TANAKA

It is certified that error appears in the above-indentified patent and that said Letters Patent is hereby corrected as shown below: ON THE TITLE PAGE:

Item [86] PCT No. "371 Date: Jan. 21, 1995" should read --371 Date: Jun. 21, 1995-- and "102(e) Date: Jan. 21, 1995" should read --Jun. 21, 1995--.

Signed and Sealed this

Twenty-fourth Day of November, 1998

Attest:

BRUCE LEHMAN

Attesting Officer

Commissioner of Patents and Trademarks